United States Patent [19]

Baxter et al.

[11] Patent Number: 4,564,882
[45] Date of Patent: Jan. 14, 1986

[54] HUMIDITY SENSING ELEMENT

[75] Inventors: Ronald D. Baxter; Paul J. Freud, both of Furlong, Pa.

[73] Assignee: General Signal Corporation, Stamford, Conn.

[21] Appl. No.: 641,534

[22] Filed: Aug. 16, 1984

[51] Int. Cl.$^4$ .............................................. H01G 5/20
[52] U.S. Cl. .................................... 361/286; 73/336.5
[58] Field of Search .......................... 73/336.5; 338/35; 361/286

[56] References Cited

U.S. PATENT DOCUMENTS 4,424,508  1/1984  Harata et al. ........................ 338/35
4,442,422  4/1984  Murata et al. .................. 73/336.5 X

FOREIGN PATENT DOCUMENTS 1413021  8/1965  France ................................. 73/336.5
148817  11/1981  Japan .................................... 361/286

Primary Examiner—Donald A. Griffin

Attorney, Agent, or Firm—Harold Huberfeld; William G. Miller, Jr.

[57] ABSTRACT

The structure consists of a substrate, a set of interdigitated electrodes deposited on the substrate surface. The electrode fingers have a period less than the substrate thickness. A first water permeable polymer film is deposited over the electrodes and a conductive mesh is formed over the first polymer film. A second polymer film is deposited over the mesh burying the mesh between the two polymer films. The spacing between openings of the mesh is less than the thickness of the second polymer film. The square of the sum of the two polymer film thicknesses is minimized so that the response time is minimized. The mesh conductivity is made greater than a minimum value so that the resistive component of the impedance is small compared with the capacitive impedance, and thus the device impedance is independent of any instabilities in the conductive mesh impedance.

10 Claims, 2 Drawing Figures

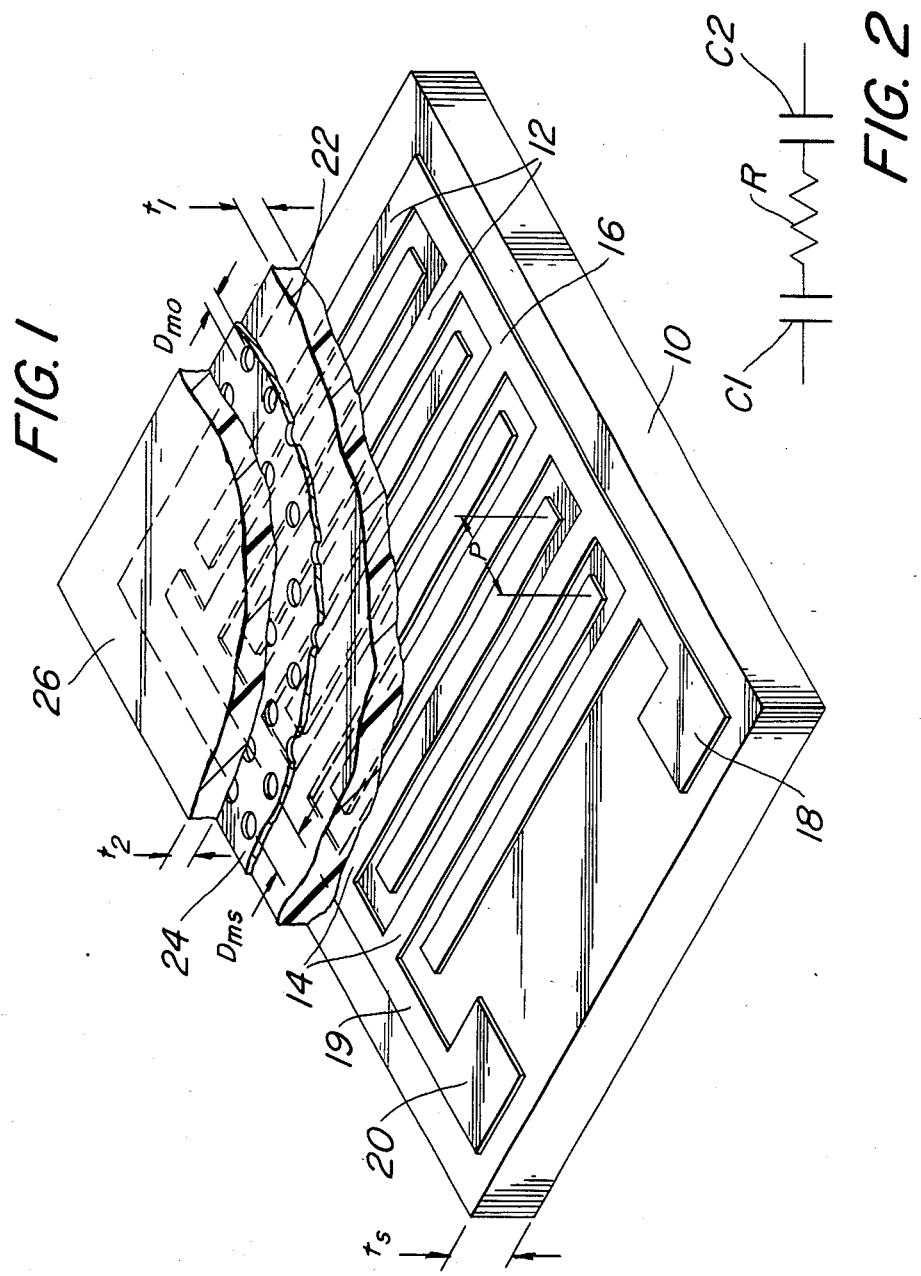

HUMIDITY SENSING ELEMENT

BACKGROUND OF THE INVENTION

This invention relates to an improved capacitance humidity sensing element for use in measuring the humidity of the atmosphere and is an improvement on U.S. Pat. No. 4,429,343, issued Jan. 31, 1984 to one of the present coinventors. This patent is hereby incorporated by reference as a part of this specification.

In the referenced patent there is described a humidity sensing element which functions by sensing changes in the dielectric constant of a thin water absorbing polymer film as induced by changes in the relative humidity of the surrounding atmosphere. As set forth in that patent, the interdigitated electrode structure underlying the polymer film is capacitively coupled through the film. Thus, the capacitance between electrodes is dependent upon the dielectric constant of the polymer film and the concentration of water molecules absorbed in the film.

The patent discloses that by using a polymer film whose thickness is greater than the period of the fingers of the interdigitated electrodes, it is possible to insure that the capacitance between the fingers will not depend upon the conditions outside of the polymer film or at its surface. This property is very important for practical devices, because it insures that the device will be independent of surface contamination or extraneous coatings on the polymer film.

In practice the minimum spacing possible between the interdigitated electrodes, in the structure of the referenced patent, is limited by the patterning techniques available. Thus, as taught by the patent, the minimum spacing between the electrodes will dictate what the minimum thickness for the polymer film can be, while still maintaining the desired independence from surface contamination. That minimum will then dictate the minimum response time for which the sensing element can be designed, for a decreased response time is obtained by decreasing the polymer thickness.

While the above mentioned patent suggests polymer thicknesses on the order of 50 microns, U.S. Pat. No. 4,164,868, issued to Suntola on Aug. 21, 1979, describes elements using a polymer film of 1 micron thickness, or less, over a two electrode arrangement, to obtain a faster response. As described in the patent, the polymer is overlayed by a thin electrically conductive water permeable layer. According to the patent, the effect of the overlay is to make the equivalent circuit between the two electrodes appear as two series capacitors in which the polymer is the dielectric and the thin conductive layer acts as the common electrode. To be complete, it would be appropriate to include in the equivalent circuit a resistance between the two capacitors in order to represent the effective resistance of the thin conductive layer. In addition, it should be noted that, the Suntola patent indicates that the thickness of the conductive layer is 0.1 to 1 microns, which would be generally impervious to water except through fractures which might be present. No method is described for making the Suntola device water permeable. If, by some means openings are provided to make the conductive layer highly permeable to water, then the conductive layer will not protect the device from the influence of contaminants on the surface, for the electrical field between the electrodes will fringe out through the conductive layer at the openings. Also, the unprotected conductive layer will be subject to the corrosive effects of atmospheric pollutants.

Other problems are presented by the thin conductive layer of the Suntola patent. The presence of that layer will tend to limit the response time of the element, for it will tend to limit the diffusion of water molecules through the conductive layer. Since metal films have very low diffusion rates, the film will have to be extremely thin. A practical limit, however, is reached in such devices when the sheet resistance of the conductive film gets to a magnitude such that the effective resistance between the two series capacitances is comparable to the impedance of those capacitances, thus causing difficulty with the capacitance measurement itself as might result from temperature changes affecting the resistance of the thin conductive layer.

It is an object of this invention to provide a structure for a humidity sensing element and a method for producing that element which will allow a minimizing of the response time while maintaining the element immune to the influences of surface contaminants.

It is a further object of this invention to provide a structure which uses an overlayed conductive film to make possible a minimization of the dielectric layer thickness to thereby minimize the response time, but which also eliminates the influence of that film on the response time of the element and maintains the response time of the element as solely a function of the thickness of the dielectric layers which cover the electrodes.

It is a further object of this invention to provide a structure which uses an overlayed conductive film to make possible a minimization of the dielectric layer thickness and thereby minimize the response time, but which also makes the response of the element independent of difficulties due to the effect of the sheet resistance of the conductive film on measurements made with the element.

SUMMARY OF THE INVENTION

In carrying out the present invention there is provided a capacitance humidity sensing element having as a support a non-conducting substrate. The support has two separate closely spaced thin metal film electrodes, which may be made up of interdigitated fingers, which are deposited on its surface with the electrode spacing having a period which is preferably less than the thickness of the substrate. A first thin dielectric film of water absorbing material covers the interdigitated electrodes and the supporting substrate. That material is one which has a dielectric constant which varies with the amount of water absorbed from the surrounding atmosphere. An electrically conductive water permeable mesh covers the first dielectric film and is constructed to have openings which are substantially evenly distributed over its surface to provide its water permeable characteristic. A second thin dielectric film of water absorbing material is placed over the mesh to protect the element from the influence of surface contaminants. In order to avoid any effect of the mesh on the response time, the average spacing between openings in the mesh is kept to a dimension less than the thickness of the first dielectric film. At the same time, the average diameter of the openings in the mesh are kept less than the thickness of the second dielectric film so as to minimize any influence from surface contaminants. The sum of the film thicknesses can be minimized to minimize the response time, and the element can be made independent of effects due to the resistance of the mesh material by assuring a minimum sheet resistance for the mesh while adhering to the constraints on the opening size and spacing.

BRIEF DESCRIPTION OF THE DRAWINGS

FIG. 1 is a perspective view of a humidity sensing element constructed in accordance with this invention with the separate layers broken away for clarity.

FIG. 2 is a circuit diagram of the equivalent circuit between any two opposing electrodes in the structure of FIG. 1.

DESCRIPTION OF THE PREFERRED EMBODIMENT

As described in U.S. Pat. No. 4,429,343, the humidity measuring element of FIG. 1 has a planar non-conducting substrate 10 which carries on its surface a deposited thin metal film electrode system made up of a first set of fingers 12 and a second set of fingers 14, all located in an interdigitated configuration. The fingers 12 are connected in parallel to a common bus 16, which is in turn connected to the contact structure 18, at which point electrical contact is made with the measuring instruments to be used.

The other fingers 14 are connected in parallel to the bus 19, which is in turn connected to the contact 20 to provide electrical connection to the measuring instrument to be used. The interdigitated fingers are shown as being spaced so that the distance between the center of adjacent fingers on the same set is "P", the period of the fingers.

The metal electrodes may be made of gold and may, for example, have 20 fingers on each electrode set with the individual fingers being 5 mils wide and the period, P, being 12 mils. The substrate supporting these electrodes may be a 20 mil thick rectangular piece of alumina which measures 100 mils by 200 mils, for example.

As shown in FIG. 1, a first thin dielectric film 22 covers the fingers 12 and 14 and the substrate supporting them. This dielectric film must be of a water absorbing material whose dielectric constant varies in proportion to the concentration of the absorbed water. Polymers are useful materials for this purpose. Among those which have been found useful are cellulose acetate butyrates and polyimides. In the structure of FIG. 1, the thickness of film 22 may be on the order of 1 micron, for example.

A thin electrically conductive mesh 24 is deposited on the top of film 22. This mesh must be permeable to water and advantageously is a non-corrosive material such as platinum, or gold or, alternatively is a stable material such as chromium or nickel. It is necessary, in order for this conductive film to be adequately permeable to water, that it have openings evenly distributed over its surface and those openings should be generally of a similar size and a similar spacing.

In order to produce the thin film 24 with the requisite openings, one may use any number of processes. For example, an impervious layer may be deposited first and then the openings may be developed by photolithographic patterning and etching or by lithographic lift off techniques. Alternatively, a sputter deposition process may be used with the opening sizes and spacing being determined by control of the process conditions. In this connection, depositions to a thicknesses of 50 to 100 angstroms provide suitable opening sizes and spacings.

As shown in FIG. 1, the film 24 is covered by a second dielectric film 26, which must also be water permeable and may advantageously be of the same material as the first dielectric film 22.

The conductive mesh 24 is characterized by openings having an average dimension $D_{mo}$ and an average opening to opening spacing of $D_{ms}$, as shown in FIG. 1. The time constant, T, of the device is generally speaking controlled by the the thickness of the polymers. Quantitatively the time constant is directly related to the square of the sum of the thicknesses, $(t1+t2)$, times the solubility of water in the polymer, S, all divided by the polymer permeability to water, P. It is important that the thickness of the first polymer layer, $t1$, be such that the lateral diffusion distance for molecules from the mesh openings to the bulk is not longer than the diffusion distance from the surface through the thickness, $t1$.

Although the electric field in the dielectric film 22 is constrained to that film by the conductive mesh 24, there will be a certain degree of fringing of the field beyond the mesh surface due to its openings. In order to contain the field totally within the water absorbing polymer, the outer dielectric film 26 must have a thickness, $t2$, larger than the mesh opening dimension $D_{mo}$. This is necessary in order for the device to be insensitive to contamination on or beyond the outer surface.

FIG. 2 illustrates the equivalent circuit which is effective between any two adjacent electrodes of opposite polarity. Thus, C1 may represent the capacitance provided by the polymer 22 between one electrode and the mesh, and C2 may represent the capacitance of the polymer 22 between the conductive mesh and an adjacent electrode. The resistance "R" then represents the equivalent resistance of that part of the mesh material which is in the field between the two electrodes under consideration. As has been mentioned, it is important to keep the value of this equivalent resistance low compared to the total impedance presented by the both capacitances, C1 and C2. More particularly, the criteria which must be met is that the ratio of the resistance to the capacitive impedance must be small compared with the ratio of humidity induced capacitance change to total capacitance. The latter ratio per 1% humidity change is typically 0.003 for useful polymer films such as polyimides or cellulose acetate butyrates. Therefore, it is desirable for the ratio of the resistance R to the total impedance of C1 and C2 to be less than 0.003. If, for example, the polymer film 22 is made of a polyimide and is 1 micron thick, and the mesh is made of chromium to a thickness such that it has a sheet resistance of 1000 ohms/square, with operation at 0.1 megahertz, it is necessary for the fingers of the electrodes to be spaced less than 0.015 cm. to maintain the ratio of resistive and capacitive impedance less than 0.003, if it is assumed that the finger spacing equals the finger width.

What is claimed is:

1. A capacitance humidity sensing element comprising:

a non-conducting substrate;

at least two separate thin metal film electrodes deposited on said substrate;

a first thin dielectric film of a water absorbing material covering said electrodes and the supporting substrate, said material being such that its dielectric constant varies with the amount of water absorbed;

an electrically conductive water permeable mesh covering said first dielectric film, said mesh having openings which are substantially evenly distributed over its surface to provide its water permeable characteristic; and a second thin film of water absorbing material covering said mesh.

2. An element as set forth in claim 1 in which
said electrodes have interdigitated fingers; and
the period of the spacing of said fingers is less than the thickness of the substrate.

3. An element as set forth in claim 1 in which
the openings in the mesh have an average diameter which is less than the thickness of said second dielectric film; and
the average spacing of said openings is less than the thickness of said first dielectric film.

4. An element as set forth in claim 3 in which
the average diameter of the openings in said mesh, the average spacing of said openings, and the sheet resistance of the mesh material are such that the resistance of the conductive path carrying the current between adjacent electrodes is small with respect to the capacitive reactance in that path due to said first dielectric film so that changes in capacitive reactance due to changes in the humidity being measured are large with respect to any changes in the resistance of the path which may occur.

5. An element as set forth in claims 3 or 4 in which
the square of the sum of the thicknesses of said first and second dielectric film is minimized while maintaining the average spacing of the openings, the average diameter of the openings and the path resistance within the desired limits.

6. An element as set forth in claims 1, 2, or 3 in which
the material of the first and second dielectric film is a polymer.

7. An element as set forth in claim 1 in which
the thickness of the mesh is between 50 and 100 angstroms.

8. A method for producing a humidity measuring element, comprising the steps of:
providing a non-conductive substrate;
depositing on said substrate two separate closely spaced interdigitated thin metal film electrodes with fingers having a period less than the thickness of said substrate;
overlaying said substrate and said electrodes with a first thin dielectric film of a water absorbing material whose dielectric constant varies with the amount of water absorbed;
depositing over said first dielectric film an electrically conductive water permeable mesh, said mesh being deposited to a thickness such that it has openings which are substantially evenly distributed over its surface to provide its water permeable characteristic; and
overlaying said mesh with a second thin dielectric film of water absorbing material.

9. A method for producing a fast responding humidity sensing element which will not be subject to influence from surface contamination, comprising the steps of:
providing a non-conductive planar substrate of a certain thickness;
depositing on said substrate two thin film interdigitated electrodes whose fingers are spaced apart by a distance such that the period of said fingers is less than the thickness of said substrate;
depositing over said interdigitated fingers a first water absorbing polymer film whose dielectric constant varies with the amount of water absorbed, said film having the thickness necessary to obtain the response time desired for the element;
depositing over said first polymer film a thin conductive mesh whose thickness is such that there are produced holes in said mesh which have an average spacing less than the thickness of said first polymer film; and
depositing over said mesh a second water absorbing polymer film whose thickness is greater than the average diameter of the holes in said mesh but is still within the thickness range required to keep the elements response time within the required range.

10. A method for producing a humidity sensing element as set forth in claim 9 in which;
the water absorbing polymer of the first and second films is a polyimide; and
the mesh is of a metal and has a thickness in the range of 50 to 100 angstroms.

* * * * *